(12) United States Patent
Piesik

(10) Patent No.: US 11,020,543 B1
(45) Date of Patent: Jun. 1, 2021

(54) DECUBITUS ULCER HEALING AIRFLOW DEVICE

(71) Applicant: Edward Piesik, Pomona, CA (US)

(72) Inventor: Edward Piesik, Pomona, CA (US)

( * ) Notice: Subject to any disclaimer, the term of this patent is extended or adjusted under 35 U.S.C. 154(b) by 0 days.

(21) Appl. No.: 15/342,121

(22) Filed: Nov. 3, 2016

(51) Int. Cl.
| | |
|---|---|
| *A61G 7/05* | (2006.01) |
| *A61M 11/02* | (2006.01) |
| *A61M 35/00* | (2006.01) |
| *A61G 7/057* | (2006.01) |

(52) U.S. Cl.
CPC .......... *A61M 11/02* (2013.01); *A61G 7/0524* (2016.11); *A61G 7/05784* (2016.11); *A61M 35/00* (2013.01)

(58) Field of Classification Search
CPC .... A61M 11/00; A61M 13/00; A61M 13/003; A61M 2205/003; F28D 2021/0028; F28D 2021/0029; H01L 23/40; H01L 23/46; H01L 23/467; F04D 29/626; F04D 23/646; B01D 2273/30; B01D 46/10; F24F 2001/0096; F24F 6/14; F24F 6/08; A61G 7/0524; A61G 7/05784
See application file for complete search history.

(56) References Cited

U.S. PATENT DOCUMENTS

| | | | |
|---|---|---|---|
| 1,882,366 A | 10/1932 | Lytton | |
| 2,268,801 A | 1/1942 | Carlton | |
| 3,500,738 A * | 3/1970 | Wenig | F04D 25/10 |
| | | | 392/382 |
| 4,799,858 A | 1/1989 | Shin-Chin | |
| 5,389,037 A * | 2/1995 | Hale | A61G 10/02 |
| | | | 128/204.18 |
| 5,862,737 A * | 1/1999 | Chiu | B01D 46/0086 |
| | | | 55/417 |
| 6,136,055 A * | 10/2000 | Stanek | B01D 46/001 |
| | | | 55/357 |
| 6,155,782 A | 12/2000 | Hsu | |
| 6,413,302 B1 * | 7/2002 | Harrison | F24F 3/16 |
| | | | 261/DIG. 88 |
| 6,596,018 B2 | 7/2003 | Endo et al. | |
| 6,694,557 B1 * | 2/2004 | Bobey | A61G 7/015 |
| | | | 5/425 |
| 7,631,377 B1 * | 12/2009 | Sanford | A47C 21/044 |
| | | | 5/413 R |
| 8,235,686 B2 | 8/2012 | Wark | |
| D669,976 S | 10/2012 | Hsu | |
| 9,308,393 B1 | 4/2016 | Olvera | |
| 2004/0031248 A1 * | 2/2004 | Lindsay | B01D 46/0023 |
| | | | 55/385.3 |

(Continued)

*Primary Examiner* — Nathan R Price
*Assistant Examiner* — Courtney B Fredrickson

(57) ABSTRACT

A decubitus ulcer healing airflow device includes a motorized airflow intake fan disposed within a housing body devised to be attached to a bed rail A tubular airflow outlet is attached to a rear side of the housing body. An air filter slideably engages an access slot and is disposed between a protective grill and an airflow intake fan. At least one strap has a central elastomeric central section engageable onto the bed rail and a pair of u-shaped outer ends. Each strap engages a respective one of a pair of strap support holders disposed on each or one of a top and bottom side of the housing body. A slotted compartment, within the airflow outlet, contains a fragrance or a vaporized medicine to assist in healing the ulcers.

6 Claims, 5 Drawing Sheets

(56) References Cited

U.S. PATENT DOCUMENTS

2006/0168925 A1* 8/2006 Whittemore ....... B01D 46/0005
  55/490
2011/0247134 A1* 10/2011 Howell ................ A61G 7/0507
  5/423

* cited by examiner

DECUBITUS ULCER HEALING AIRFLOW DEVICE

CROSS-REFERENCE TO RELATED APPLICATIONS

Not Applicable

FEDERALLY SPONSORED RESEARCH OR DEVELOPMENT

Not Applicable

INCORPORATION BY REFERENCE OF MATERIAL SUBMITTED ON A COMPACT DISK

Not Applicable

BACKGROUND OF THE INVENTION

Various types of portable fans are known in the prior art. However, what is needed and what the present device provides is a decubitus ulcer healing airflow device including a motorized airflow intake fan disposed within a housing body devised to be attached to a bed rail and a tubular airflow outlet attached to a rear side of the housing body to direct airflow onto and to ventilate and dry an area or areas with decubitus ulcers.

FIELD OF THE INVENTION

The present invention relates to portable fans, and more particularly, to a decubitus ulcer healing airflow device attachable to a bedridden patient's bed.

SUMMARY OF THE INVENTION

The general purpose of the present decubitus ulcer healing airflow device, described subsequently in greater detail, is to provide a decubitus ulcer healing airflow device which has many novel features that result in a decubitus ulcer healing airflow device which is not anticipated, rendered obvious, suggested, or even implied by prior art, either alone or in combination thereof. To accomplish this, the present decubitus ulcer healing airflow device is provided to ventilate and dry an area in which a decubitus ulcer is present in order to heal the decubitus ulcer. The device may also assist in preventing decubitus ulcers from developing by ventilating and drying an area or areas prone to such ulcers.

The instant decubitus ulcer healing airflow device includes a housing body having top and bottom sides, right and left sides, a continuous front perimeter, a rear side, and a cavity continuously disposed therein. A protective grill is centrally disposed within the front frame. A hollow tubular airflow outlet is provided and has a forward side centrally disposed on rear side and a rearward side. A motorized airflow intake fan, which has a plurality of blades, is disposed within the cavity. A variable speed motor is disposed within the cavity. The airflow intake fan is in operational communication with the motor, which is in operational communication with a power source. An on-off variable control switch, disposed on the housing body, is in operational communication with the motor and controls the rotational speed of the airflow intake fan blades. An air filter slideably engages an access slot into the cavity and is disposed between the protective grill and the airflow intake fan. A grip notch, disposed directly adjacent the access slot, assists with the insertion and removal of the air filter into and from the access slot, respectively. Airflow taken in through the airflow intake fan is configured to pass through the tubular airflow outlet and onto at least one decubitus ulcer of a patient toward which the airflow of the airflow intake fan is directed. Airflow taken in through the airflow intake fan is further configured to pass through the air filter prior to passage of the airflow through the airflow intake fan.

A pair of strap support holders is disposed on each or one of the top side and the bottom side in a position parallel to the rear side and to each other. At least one strap has a central elastomeric central section and a pair of u-shaped outer ends opposite each other is provided. Each of the outer ends engages a respective one of the pair of strap support holders. The central section is disposed in a gap between the pair of strap support holders. The central section of the at least one strap is engageable onto a bed rail.

A slotted compartment, disposed within the tubular airflow outlet proximal the rearward side, has a plurality of apertures therein and is configured to store one of a fragrance, a vaporized medicine, and one of a plurality of gases including oxygen. Airflow through the air filter and the airflow intake fan is further configured to pass through the slotted compartment prior to passage of the airflow through the tubular airflow outlet.

The housing body is envisioned to have a height and a width in a range of approximately 10 inches to 20 inches, although such dimensions may be varied to accommodate other situations in which the present device may be employed. The present device is relatively lightweight for transport, storage, and handling and also for attachment to a bed rail. Sound suppression elements may also be provided to reduce potential noise produced by the airflow intake fan, including insulation material within the housing body or a noise-reduction airflow intake fan. The u-shaped outer ends of the straps may be replaced or include hook and loop fastening, clamps, clips, snaps or other fasteners to ensure complete attachment to a bed rail. Either or both of the forward side and the rearward side of the tubular airflow outlet may also include such fasteners to ensure stable support thereof and complete and stable attachment to the housing body. Thus has been broadly outlined the more important features of the present decubitus ulcer healing airflow device so that the detailed description thereof that follows may be better understood and in order that the present contribution to the art may be better appreciated.

BRIEF DESCRIPTION OF THE DRAWINGS

Figures

DETAILED DESCRIPTION OF THE DRAWINGS

Figure 1:
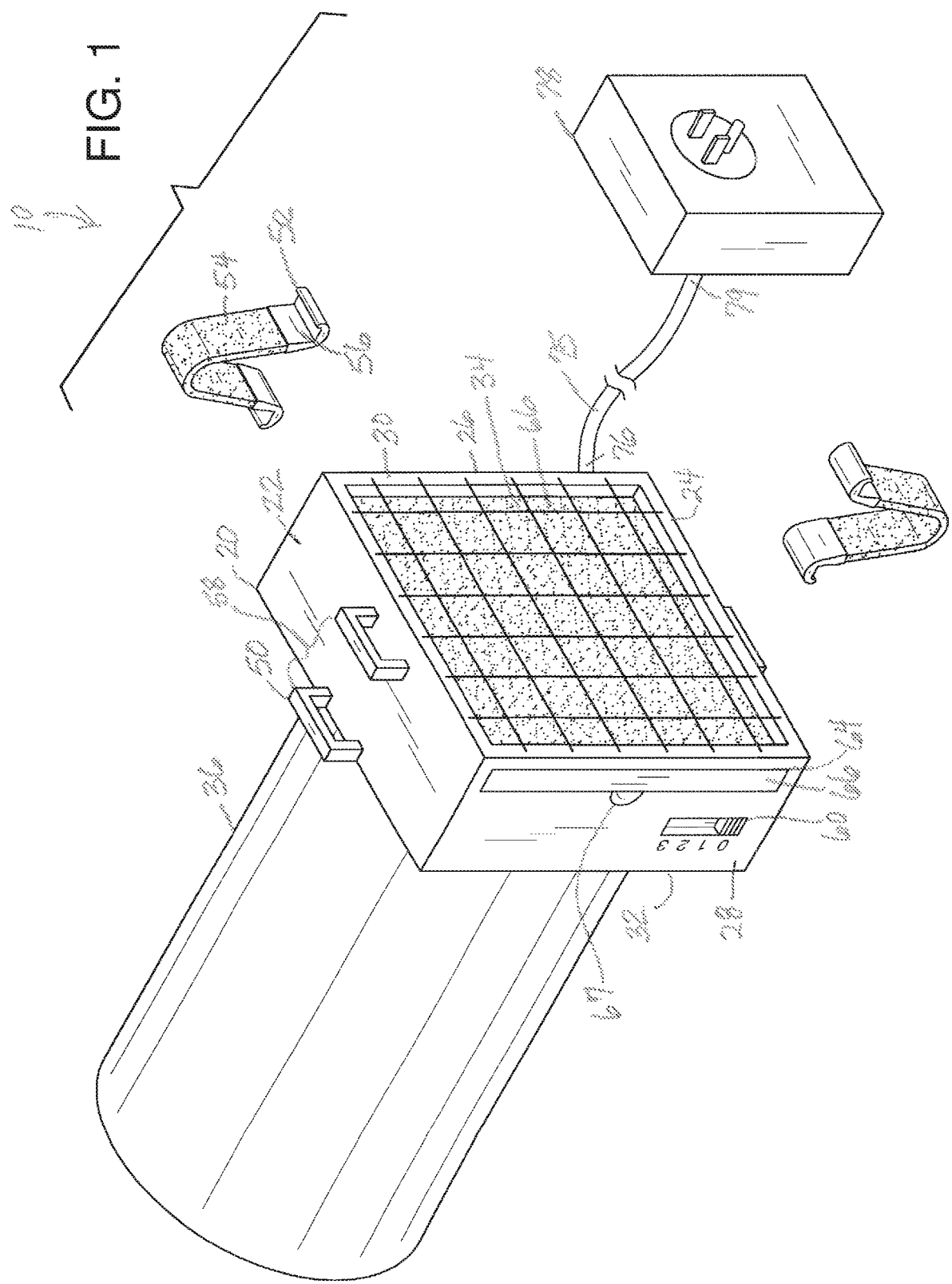
FIG. 1 is an isometric view.
Figure 2:
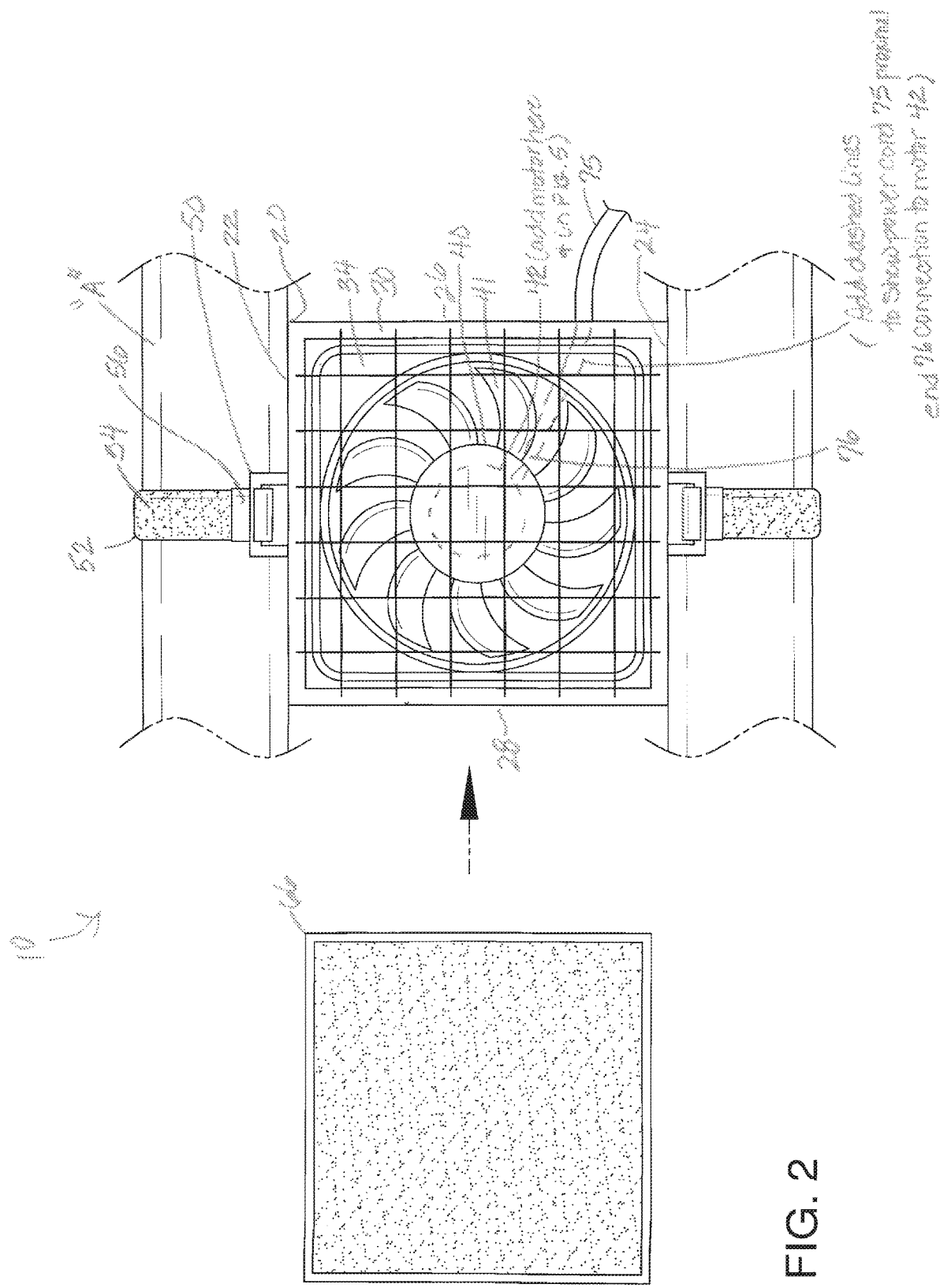
FIG. 2 is a front elevation view.
Figure 3:
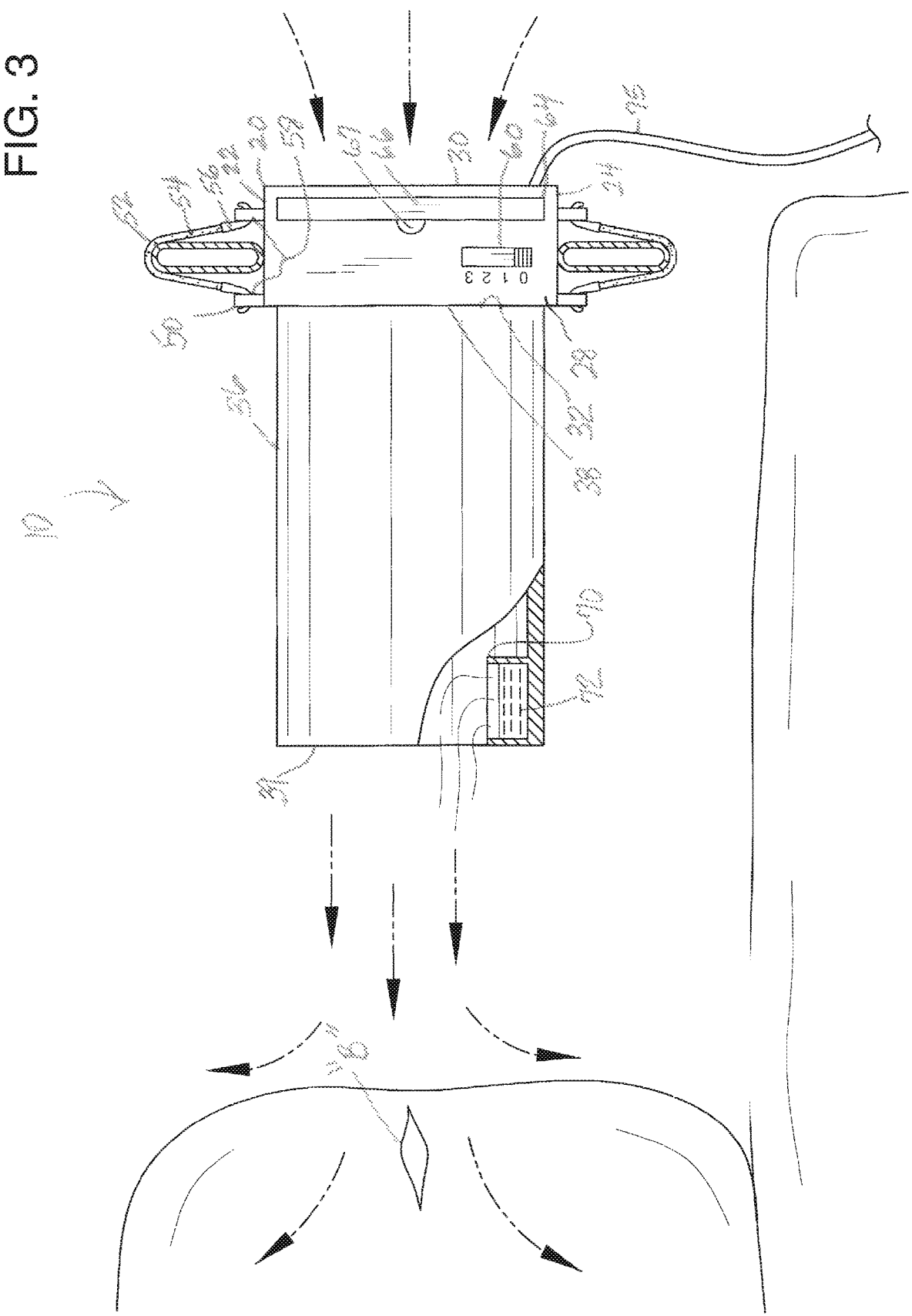
FIG. 3 is a side elevation view.
Figure 4:
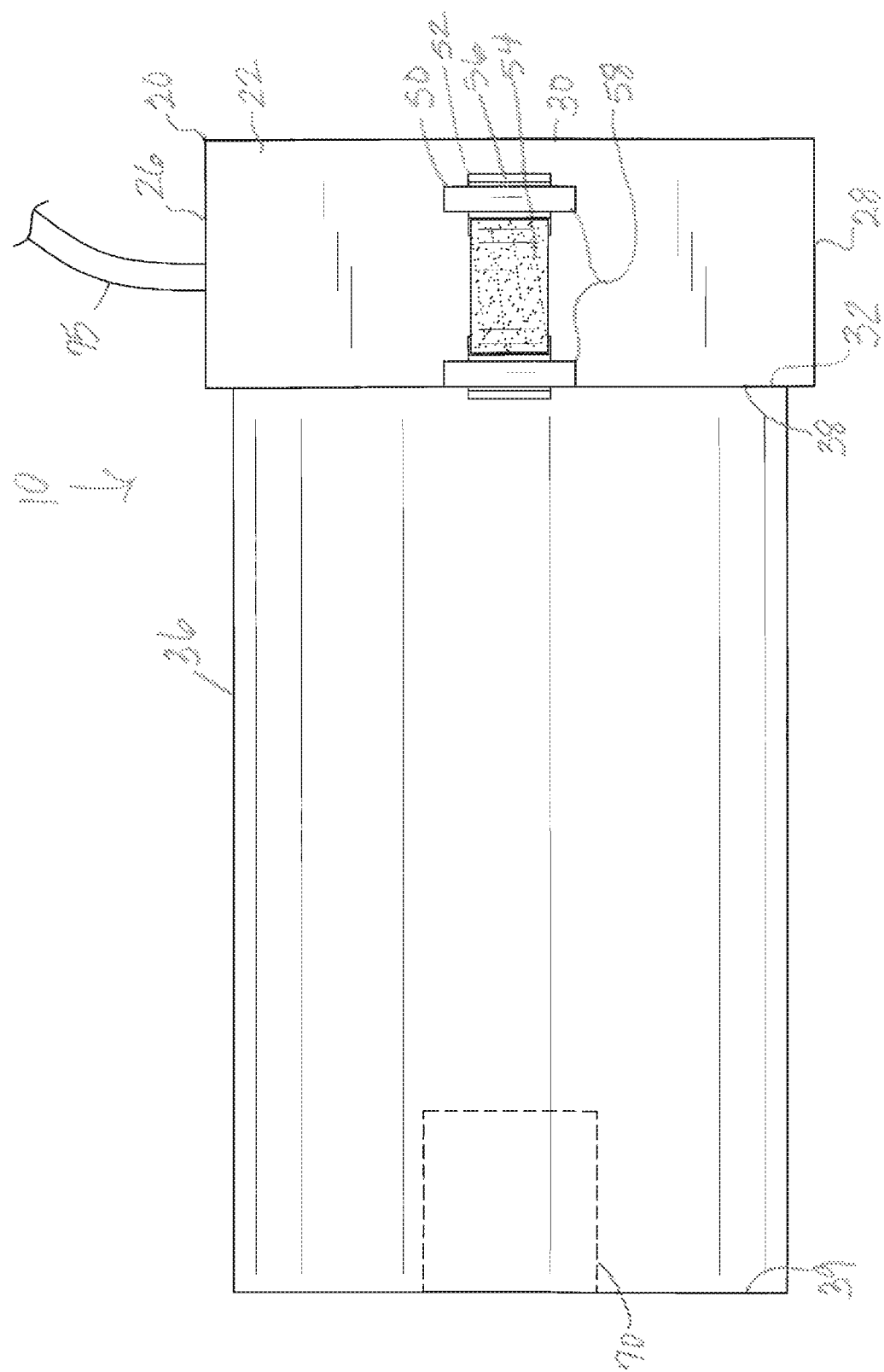
FIG. 4 is a top plan view.
Figure 5:
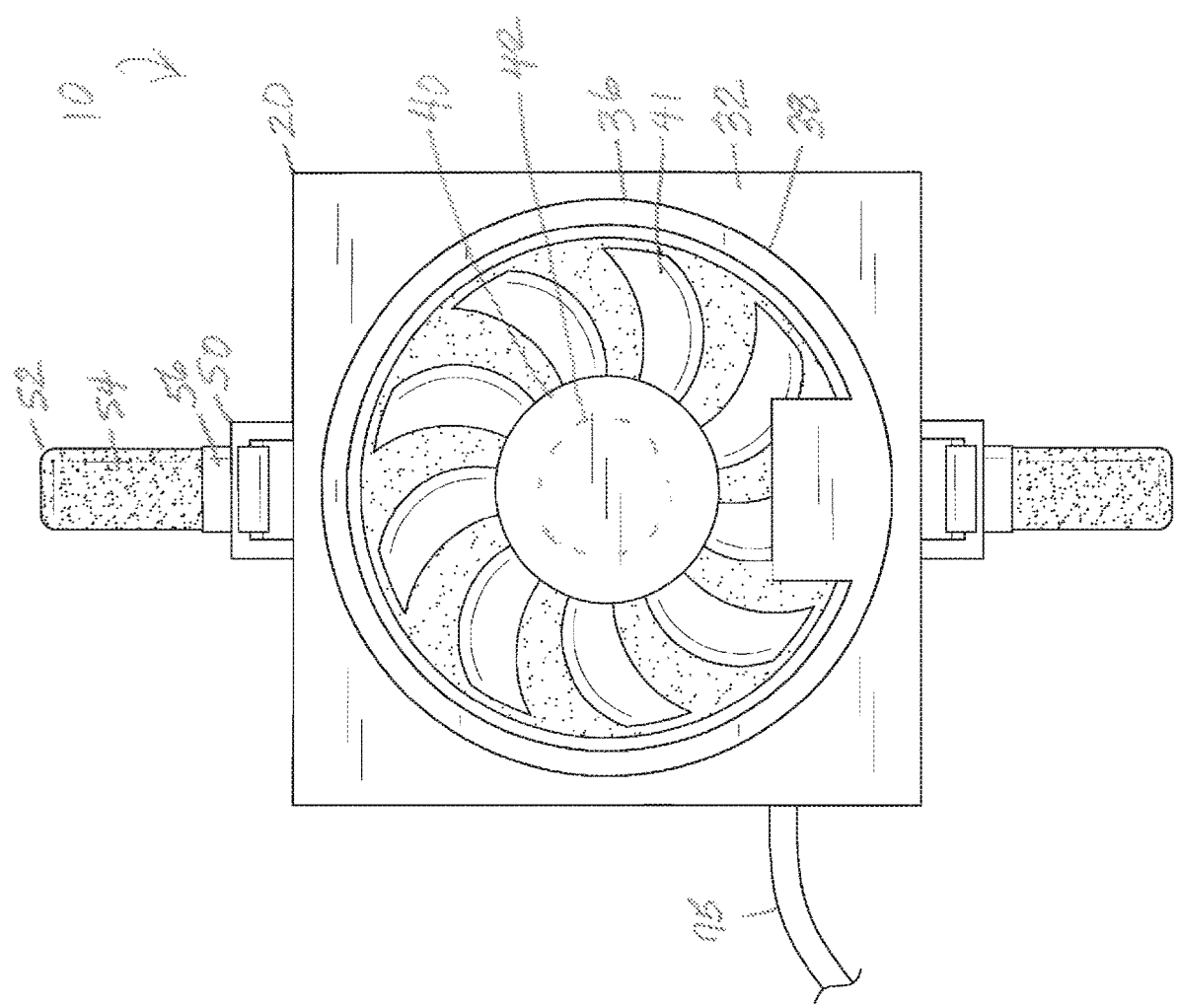
FIG. 5 is rear elevation view.

With reference now to the drawings, and in particular FIGS. 1 through 5 thereof, an example of the instant decubitus ulcer healing airflow device employing the principles and concepts of the present decubitus ulcer healing airflow device and generally designated by the reference number 10 will be described.

Referring to FIGS. 1 through 5 the present decubitus ulcer healing airflow device 10 is illustrated. The decubitus ulcer healing airflow device 10 includes a housing body 20. The housing body 20 has a top side 22, a bottom side 24, a right side 26, a left side 28, a continuous front perimeter 30, a rear side 32, and a cavity 34 defined by the top side 22, the bottom side, the right side 26, the left side 28, the front frame 30, and the rear side 32. A protective grill 34 is centrally disposed within the front frame 30.

A hollow tubular airflow outlet 36 is provided and has a forward side 38 centrally disposed on rear side 32 and a rearward side 39. A motorized airflow intake fan 40, which has a plurality of blades 41, is disposed within the cavity 34. A variable speed motor 42 is disposed within the cavity 34. The airflow intake fan 40 is in operational communication with the motor 42, which is in operational communication with a power source 44. The power source 44 is electricity, as shown in the Figures, provided through an electrical power cord 75 connected to the motor 42 at a proximal end 76 of the electrical power cord 75 and an electrical plug 78 at a distal end 79 of the electrical power cord 75. However, the motor 42 can alternately be battery-powered.

A pair of strap support holders 50 is disposed on each of the top side 22 and the bottom side 24 in a position parallel to the rear side 32 and to each other. At least one strap 52 has a central elastomeric central section 54 and a pair of u-shaped outer ends 56 opposite each other is provided. Each of the outer ends 56 engages a respective one of the pair of strap support holders 50. The central section 54 is disposed in a gap 58 between the pair of strap support holders 50. The central section 54 of the at least one strap 52 is engageable onto a bed rail "A".

An on-off variable control switch 60 is disposed on the housing body 20. The control switch 60 is in operational communication with the motor 42 and controls the rotational speed of the airflow intake fan 40 blades 41.

An access slot 64 is disposed in one of the right side 26 and the left side 28 of the housing body 20. An air filter 66 is disposed between the protective grill 34 and the airflow intake fan 40. The air filter 66 slideably engages the access slot 64 into the cavity 34. A grip notch 67 is disposed directly adjacent the access slot 64. The grip notch 67 is configured to assist insertion and removal of the air filter 66 into and from the access slot 64, respectively.

Airflow taken in through the airflow intake fan 40 is configured to pass through the tubular airflow outlet 36 and onto at least one decubitus ulcer "B" of a patient toward which the airflow of the airflow intake fan 40 is directed. Airflow taken in through the airflow intake fan 40 is further configured to pass through the air filter 66 prior to passage of the airflow through the airflow intake fan 40.

A slotted compartment 70 is disposed within the tubular airflow outlet 36 proximal the rearward side 39. The slotted compartment 70 has a plurality of apertures 72 therein. The slotted compartment 70 is configured to store one of a fragrance, a vaporized medicine, and one of a plurality of gases including oxygen. Airflow through the air filter 66 and the airflow intake fan 40 is further configured to pass through the slotted compartment 70 prior to passage of the airflow through the tubular airflow outlet 36.

What is claimed is:

1. A decubitus ulcer healing airflow system comprising:
   a bed having a bed rail;
   a housing body having a top side, a bottom side, a right side, a left side, a continuous front perimeter, a rear side, and a cavity defined by the top side, the bottom side, the right side, the left side, the front perimeter, and the rear side;
   a protective grill centrally disposed within the front perimeter;
   a hollow tubular airflow outlet having a forward side centrally disposed on the rear side and a rearward side;
   a motorized airflow intake fan disposed within the cavity, the airflow intake fan having a plurality of blades;
   a variable speed motor disposed within the cavity, the airflow intake fan being in operational communication with the motor, the motor being in operational communication with a power source;
   a pair of strap support holders being disposed on the top side in a position parallel to the rear side, said pair of strap support holders being parallel to each other;
   at least one strap having an elastomeric central section and a pair of u-shaped outer ends opposite each other, each of the outer ends engaging a respective one of the pair of strap support holders, the central section disposed in a gap between the pair of strap support holders; and
   an on-off variable control switch disposed on the housing body, the control switch in operational communication with the motor wherein the central section is engageable atop the bed rail such that airflow taken in through the airflow intake fan is configured to pass through the tubular airflow outlet and onto at least one decubitus ulcer of a patient toward which the airflow of the airflow intake fan is directed.

2. The decubitus ulcer healing airflow system of claim 1 comprising:
   an access slot disposed in one of the right side and the left side of the housing body; and
   an air filter disposed between the protective grill and the airflow intake fan, the air filter slideably engaging the access slot into the cavity;
   wherein airflow taken in through the airflow intake fan is further configured to pass through the air filter prior to passage of the airflow through the airflow intake fan.

3. The decubitus ulcer healing airflow system of claim 1 comprising:
   a slotted compartment disposed within the tubular airflow outlet proximal the rearward side, the slotted compartment having a plurality of apertures therein;
   wherein the slotted compartment is configured to store one of a fragrance, a vaporized medicine, and one of a plurality of gases including oxygen; and
   wherein airflow through the air filter and the airflow intake fan is further configured to pass through the slotted compartment prior to passage of the airflow through the tubular airflow outlet.

4. The decubitus ulcer airflow system of claim 1 wherein the power source is electricity provided through an electrical power cord connected to the motor at a proximal end of the electrical power cord and an electrical plug at a distal end of the electrical power cord.

5. A decubitus ulcer healing airflow system comprising:
   a bed having a bed rail;
   a housing body having a top side, a bottom side, a right side, a left side, a continuous front perimeter, a rear side, and a cavity defined by the top side, the bottom side, the right side, the left side, the front perimeter, and the rear side;
   a protective grill centrally disposed within the front perimeter;

a hollow tubular airflow outlet having a forward side centrally disposed on the rear side and a rearward side;

a motorized airflow intake fan disposed within the cavity, the airflow intake fan having a plurality of blades;

a variable speed motor disposed within the cavity, the airflow intake fan being in operational communication with the motor, the motor being in operational communication with a power source;

a plurality of strap support holders, said strap support holders being arranged into two pairs with each pair being disposed on a respective one of the top side and the bottom side in a position parallel to the rear side and to each other;

at least one strap having an elastomeric central section and a pair of u-shaped outer ends opposite each other, each of the outer ends engaging a respective one of the pair of strap support holders, the central section disposed in a gap between the pair of strap support holders;

an on-off variable control switch disposed on the housing body, the control switch in operational communication with the motor;

an access slot disposed in one of the right side and the left side of the housing body;

an air filter disposed between the protective grill and the airflow intake fan, the air filter slideable engaging the access slot into the cavity;

a grip notch disposed directly adjacent the access slot, wherein the grip notch is configured to assist insertion and removal of the air filter into and from the access slot, respectively;

wherein the central section of the at least one strap is engageable onto the bed rail such that airflow taken in through the airflow intake fan is configured to pass through the tubular airflow outlet and onto at least one decubitus ulcer of a patient toward which the airflow of the airflow intake fan is directed;

wherein airflow taken in through the airflow intake fan is further configured to pass through the air filter prior to passage of the airflow through the airflow intake fan;

a slotted compartment disposed within the tubular airflow outlet proximal the rearward side, the slotted compartment having a plurality of apertures therein;

wherein the slotted compartment is configured to store one of a fragrance, a vaporized medicine, and one of a plurality of gases including oxygen; and wherein airflow through the air filter and the airflow intake fan is further configured to pass through the slotted compartment prior to passage of the airflow through the tubular airflow outlet.

6. The decubitus ulcer airflow system of claim 5 wherein the power source is electricity provided through an electrical power cord connected to the motor at a proximal end of the electrical power cord and an electrical plug at a distal end of the electrical power cord.

\* \* \* \* \*